United States Patent
Shoji

(10) Patent No.: US 11,160,443 B2
(45) Date of Patent: Nov. 2, 2021

(54) ELECTRONIC ENDOSCOPE DEVICE FOR CHANGING OBSERVATION IMAGE BRIGHTNESS

(71) Applicant: HOYA CORPORATION, Tokyo (JP)

(72) Inventor: Takaaki Shoji, Tokyo (JP)

(73) Assignee: HOYA CORPORATION, Tokyo (JP)

(*) Notice: Subject to any disclaimer, the term of this patent is extended or adjusted under 35 U.S.C. 154(b) by 155 days.

(21) Appl. No.: 16/489,806

(22) PCT Filed: Mar. 8, 2018

(86) PCT No.: PCT/JP2018/009003
§ 371 (c)(1),
(2) Date: Aug. 29, 2019

(87) PCT Pub. No.: WO2018/180339
PCT Pub. Date: Apr. 10, 2018

(65) Prior Publication Data
US 2019/0380567 A1    Dec. 19, 2019

(30) Foreign Application Priority Data

Mar. 30, 2017    (JP) .............................. JP2017-069036

(51) Int. Cl.
*A61B 1/05*        (2006.01)
*A61B 1/06*        (2006.01)
(Continued)

(52) U.S. Cl.
CPC .............. *A61B 1/05* (2013.01); *A61B 1/0002* (2013.01); *A61B 1/0661* (2013.01); *A61B 1/00009* (2013.01); *A61B 1/045* (2013.01)

(58) Field of Classification Search
None
See application file for complete search history.

(56) References Cited

U.S. PATENT DOCUMENTS 6,425,858 B1    7/2002  Minami
7,460,779 B2 *  12/2008 Nakata ............... H04N 5/23212
                                                  396/96
(Continued)

FOREIGN PATENT DOCUMENTS

JP    2000-270256 A    9/2000
JP    2011-030985 A    2/2011
(Continued)

OTHER PUBLICATIONS

International Search Report issued in WIPO Patent Application No. PCT/JP2018/009003, dated Apr. 10, 2018.

*Primary Examiner* — Michael J Carey
*Assistant Examiner* — Minqiao Huang
(74) *Attorney, Agent, or Firm* — Greenblum & Bernstein, P.L.C.

(57) ABSTRACT

An electronic endoscope device is provided.
An electronic endoscope device for obtaining an imaging signal from an imaging device for imaging an object and outputting an image based on the obtained imaging signal is provided with a brightness calculation unit that calculates brightness of the image, and a control unit that changes an exposure time in the imaging device exponentially so that the brightness calculated by the brightness calculation unit approaches set brightness.

4 Claims, 5 Drawing Sheets

(51) Int. Cl.
*A61B 1/00* (2006.01)
*A61B 1/045* (2006.01)

(56) References Cited

U.S. PATENT DOCUMENTS

| | | | |
|---|---|---|---|
| 7,496,290 B2* | 2/2009 | Nakata | G02B 7/282 |
| | | | 348/349 |
| 7,512,332 B2* | 3/2009 | Iwamoto | H04N 5/232127 |
| | | | 396/147 |
| 7,725,013 B2 | 5/2010 | Sugimoto et al. | |
| 7,943,034 B2* | 5/2011 | Diamond | G01N 27/3273 |
| | | | 205/792 |
| 8,947,514 B2 | 2/2015 | Shibasaki | |
| 9,949,625 B2 | 4/2018 | Fukuda | |
| 2013/0096376 A1* | 4/2013 | Takei | A61B 1/063 |
| | | | 600/103 |
| 2013/0169775 A1* | 7/2013 | Ono | A61B 1/00009 |
| | | | 348/68 |
| 2013/0208101 A1* | 8/2013 | Ono | A61B 1/00045 |
| | | | 348/65 |
| 2013/0245410 A1 | 9/2013 | Saito | |
| 2013/0271587 A1* | 10/2013 | Tsuyuki | A61B 1/00009 |
| | | | 348/71 |
| 2014/0104403 A1* | 4/2014 | Ogasawara | A61B 1/00045 |
| | | | 348/68 |
| 2014/0171737 A1 | 6/2014 | Kagaya et al. | |
| 2014/0203170 A1* | 7/2014 | Ono | A61B 1/045 |
| | | | 250/208.1 |
| 2014/0340496 A1* | 11/2014 | Okawa | H04N 5/243 |
| | | | 348/65 |
| 2015/0173595 A1* | 6/2015 | Takekoshi | A61B 1/045 |
| | | | 600/317 |
| 2016/0269611 A1* | 9/2016 | Kutsuma | H04N 5/243 |
| 2017/0172387 A1* | 6/2017 | Matsui | A61B 1/00009 |
| 2019/0142240 A1 | 5/2019 | Hayashi | |

FOREIGN PATENT DOCUMENTS

| | | |
|---|---|---|
| JP | 2012-085790 A | 5/2012 |
| JP | 2013-188365 A | 9/2013 |
| JP | 2014-117414 A | 6/2014 |

* cited by examiner

FIG. 3

| ADDRESS | EXPOSURE TIME (sec) |
|---|---|
| 0 | 1/60 |
| 1 | 1/60.37310579 |
| 2 | 1/60.74853172 |
| 3 | 1/61.12629221 |
| 4 | 1/61.50640177 |
| 5 | 1/61.88887502 |
| ⋮ | ⋮ |
| n | $1/60 \times 0.99382^n$ |
| ⋮ | ⋮ |
| 1023 | 1/34067.55812 |

ELECTRONIC ENDOSCOPE DEVICE FOR CHANGING OBSERVATION IMAGE BRIGHTNESS

TECHNICAL FIELD

The present invention relates to an electronic endoscope device.

BACKGROUND ART

An endoscope system for observing a lumen such as the esophagus or intestine of a person is known. The endoscope system of this type is provided with an endoscope processor which processes an image of an object imaged by an electronic scope. The endoscope processor performs image processing such as color conversion processing and noise reduction processing on a pixel signal in order to allow a monitor device to display an observation image easily viewable by an operator.

Also, when allowing the monitor device to display the observation image, the endoscope processor calculates brightness of an image based on an image signal input from the electronic scope, and controls aperture of a light source and an exposure time of an imaging device on the basis of the calculated brightness, thereby adjusting brightness of the observation image (refer to, for example, Patent Literature 1).

CITATION LIST

Patent Literature

Patent Literature 1: JP 2000-270256 A

SUMMARY OF INVENTION

Technical Problem

However, in the technology disclosed in Patent Literature 1, a target value of the exposure time and a speed (transition speed) to change the brightness cannot be set finely, and there is a problem that the brightness of the observation image might drastically change.

An object of the present invention is to provide an electronic endoscope device capable of flexibly changing the brightness in the observation image.

Solution to Problem

An electronic endoscope device according to an aspect of the present invention is an electronic endoscope device for obtaining an imaging signal from an imaging device for imaging an object and outputting an image based on the obtained imaging signal provided with a brightness calculation unit that calculates brightness of the image, and a control unit that changes an exposure time in the imaging device exponentially so that the brightness calculated by the brightness calculation unit approaches set brightness.

Advantageous Effects of Invention

According to the above, it is possible to flexibly change the brightness in the observation image.

BRIEF DESCRIPTION OF DRAWINGS

FIG. 3 is a conceptual diagram illustrating an example of a look-up table.

DESCRIPTION OF EMBODIMENTS

Hereinafter, the present invention is specifically described with reference to the drawings illustrating an embodiment thereof.

Figure 1:
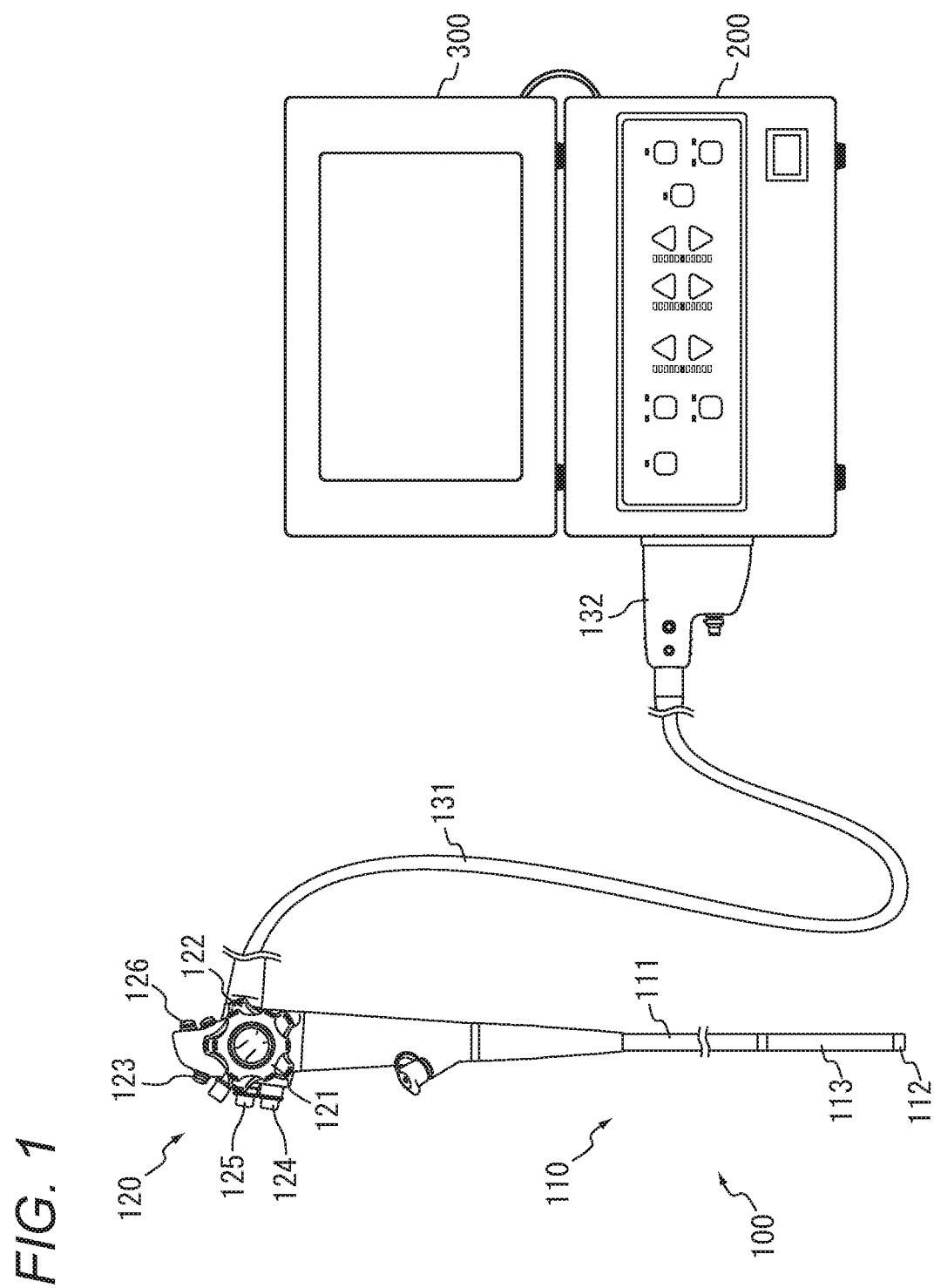
FIG. 1 is a schematic diagram for illustrating a schematic configuration of an electronic endoscope device according to this embodiment.

FIG. 1 is a schematic diagram for illustrating a schematic configuration of an electronic endoscope device according to this embodiment. The electronic endoscope device according to this embodiment, is provided with an electronic scope 100 for taking an image of an object, a processor device 200 for processing an image signal from the electronic scope 100 to generate a moving image and a still image, and a monitor device 300 for reproducing the moving image and the still image generated by the processor device 200.

The electronic scope 100 is provided with an insertion unit 110 and an operation unit 120. The insertion unit 110 is provided with a flexible tube 111 covered with a flexible sheath (outer shell), and a distal end portion 112 covered with a hard resin casing is connected to a distal end of the flexible tube 111. A bending portion 113 located in a connection site between the flexible tube 111 and the distal end portion 112 is configured to be bent in vertical and horizontal directions by operation from the operation unit 120. This bending mechanism is a well-known mechanism incorporated in a general electronic scope, and the bending portion 113 is configured to be bent by tugging of an operation wire interlocked with the operation of the operation unit 120 (specifically, rotational operation of bending operation knobs 121 and 122). By changing a direction of the distal end portion 112 according to bending operation by the above-described operation, an imaging area by the electronic scope 100 moves.

In addition to the bending operation knobs 121 and 122 for bending the bending portion 113, the operation unit 120 is provided with an air/water supply button 123 for ejecting gas and liquid from the distal end portion 112, a freeze button 124 for switching an observation image to moving image display or still image display, a zoom button 125 for instructing to enlarge/reduce the observation image displayed on the monitor device 300, a switching button 126 for switching between normal light and treatment light and the like.

A connector unit 132 is also connected to the operation unit 120 via a universal cord 131. The electronic scope 100 is electrically and optically connected to the processor device 200 via the connector unit 132.

The processor device 200 is a device provided with a signal processing device for processing the image signal from the electronic scope 100 and a light source device for irradiating a body cavity to which natural light does not reach via the electronic scope 100 in an integral manner. In another embodiment, the signal processing device and the light source device may be configured separately.

The processor device 200 is provided with a connector unit 210 (refer to FIG. 2) corresponding to the connector unit 132 of the electronic scope 100. The connector unit 210 has a connecting structure corresponding to the connector unit 132 of the electronic scope 100 and electrically and optically connects the electronic scope 100.

The monitor device 300 is a device connected to the processor device 200 for displaying the moving image or the still image output from the processor device 200. The monitor device 300 is a general-purpose display device such as a liquid crystal display device. In another embodiment, the monitor device 300 may be a device integral with the processor device 200.

Figure 2:
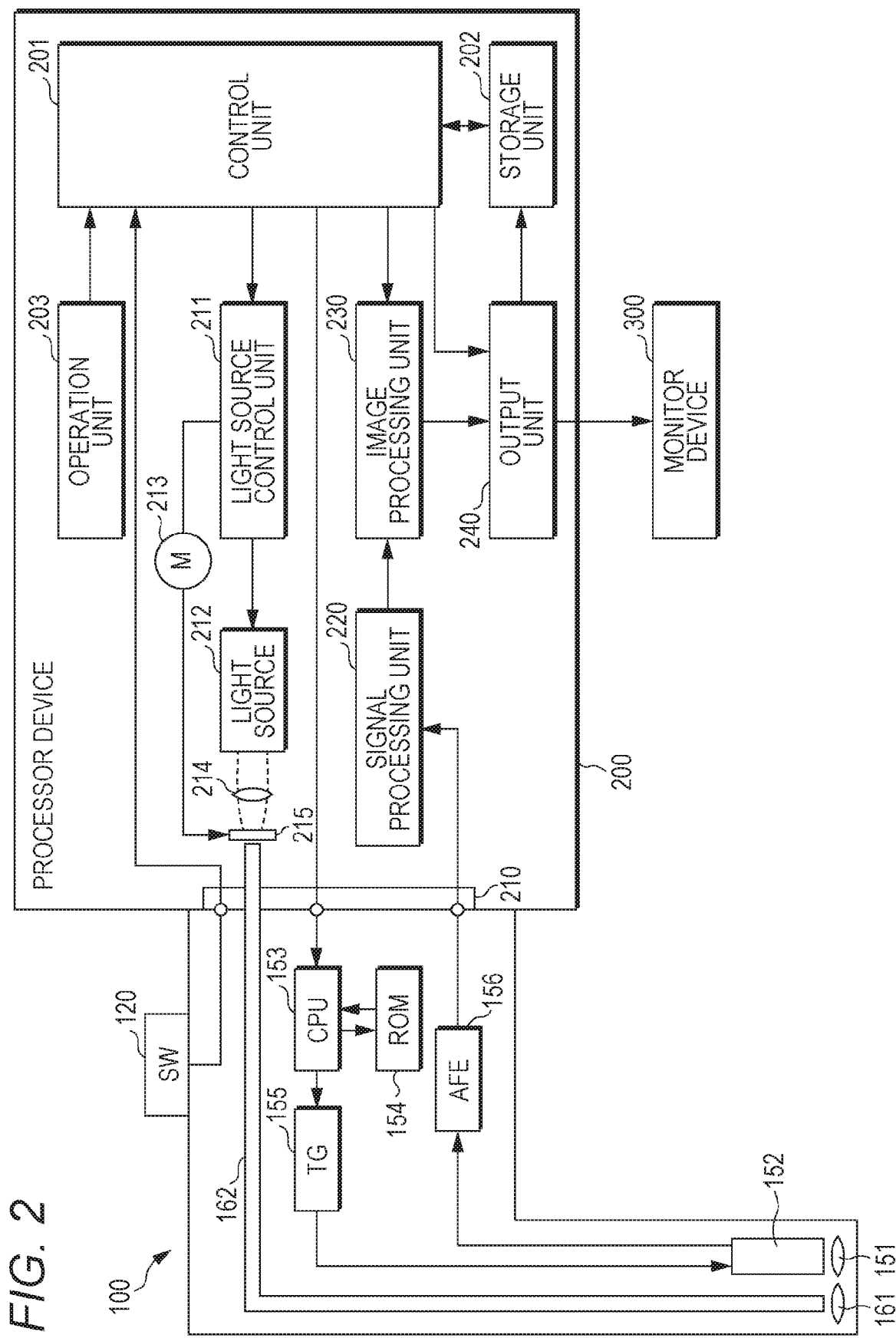
FIG. 2 is a block diagram for illustrating a configuration of a control system of the electronic endoscope device.

FIG. 2 is a block diagram for illustrating a configuration of a control system of the electronic endoscope device. The electronic scope 100 is provided with an objective optical system 151, a solid-state imaging device 152, an illumination lens 161, a light guide 162 and the like.

The objective optical system 151 and the solid-state imaging device 152 are arranged inside an observation window (not illustrated) provided on the distal end portion 112 of the electronic scope 100. The objective optical system 151 is formed of a lens group including an objective lens and a prism. The solid-state imaging device 152 photoelectrically converts an image of the object formed on an imaging surface by the objective optical system 151.

The solid-state imaging device 152 is an imaging device such as a charge-coupled device (CCD) or a complementary metal oxide semiconductor (CMOS). To the solid-state imaging device 152, a central processing unit (CPU) 153, a read only memory (ROM) 154, a timing generator (TG) 155, an analog signal processing circuit (AFE) 156 and the like are connected. The CPU 153 drives the TG 155 on the basis of a control signal input from the processor device 200. The CPU 153 also controls an exposure time of the solid-state imaging device 152 with reference to information stored in the ROM 154. The TG 155 provides a clock signal to the solid-state imaging device 152. The solid-state imaging device 152 accumulates signal charges of respective colors of RGB to perform imaging operation at a predetermined frame rate according to the clock signal input from the TG 155 and the exposure time controlled by the CPU 153.

The image signal output from the solid-state imaging device 152 is an analog signal and is subjected to noise processing and gain correction processing by the AFE 156. The AFE 156 includes a correlated double sampling (CDS) circuit, an automatic gain adjusting (AGC) circuit, and an A/D converter. The CDS performs the correlated double sampling processing on the image signal output from the solid-state imaging device 152 to remove noise generated by driving of the solid-state imaging device 152. The AGC amplifies the image signal from which the noise is removed by the CDS. The A/D converter converts the image signal amplified by the AGC into a digital image signal having a predetermined hit number. The AFE 156 outputs the image signal after the A/D conversion to the processor device 200.

Note that, in another embodiment, the electronic scope 100 may output an analog imaging signal output from the solid-state imaging device 152 to the processor device 200 and convert the same into a digital imaging signal in the processor device 200.

The electronic scope 100 is also provided with the illumination lens 161 and the light guide 162. The illumination lens 161 is arranged inside an illumination window provided at the distal end portion 112 of the electronic scope 100. The light guide 162 formed of, for example, a plurality of quartz optical fibers is arranged inside the insertion unit 110, the operation unit 120, the universal cord 131, and the connector unit 132. The illumination light output from the processor device 200 is guided by the light guide 162, diffused by the illumination lens 161, and then applied to the object through the illumination window.

The processor device 200 is provided with a control unit 201, a storage unit 202, an operation unit 203, a light source control unit 211, a signal processing unit 220, an image processing unit 230, an output unit 240 and the like.

The control unit 201 is provided with, for example, a CPU, a ROM, a random access memory (RAM) and the like, and a control program stored in advance in the ROM is developed on the RAM and executed by the CPU, so that an entire device is allowed to serve as a part of the electronic endoscope device according to the present invention.

Note that, the control unit 201 is not limited to the above-described configuration, and may be one or a plurality of processing circuits including a single-core CPU, a multi-core CPU, a microcomputer, a volatile or non-volatile memory and the like. The control unit 201 may also have functions such as a clock which outputs information related to a current time, a timer which measures an elapsed time from when a measurement starting instruction is provided to when a measurement ending instruction is provided, and a counter which counts the number.

The storage unit 202 is formed of, for example, a non-volatile memory such as an erasable programmable read only memory (EPROM) or a recording device provided with a hard disk, and stores data generated in the processor device 200, externally input data and the like. In another embodiment, the storage unit 202 is a portable recording medium such as a universal serial bus (USB) memory and a secure digital (SD) card, and may be attachable to and removable from the processor device 200.

The operation unit 203 is an input device such as an operation panel including various switches and buttons provided on a casing of the processor device 200, a mouse and a keyboard connected to the processor device 200 and the like. The operation unit 203 outputs an operation signal according to the operation of the operator to the control unit 201. The control unit 201 operates each unit of the processor device 200 according to the operation signal output from the operation unit 203 and an operation signal output from the operation unit 120 provided in the electronic scope 100.

The light source control unit 211 is a control circuit for controlling driving of a light source 212 and a motor 213 under the control of the control unit 201. The light source 212 is a high-intensity lamp such as a xenon lamp, a halogen lamp, or a metal halide lamp, and emits light having a spectrum extending from a visible light region to an infrared light region. The light emitted from the light source 212 is condensed by a condenser lens 214 and converted into light having an appropriate characteristic via a rotary turret 215 equipped with a filter. The motor 213 is connected to the turret 215 via a transmission mechanism (not illustrated) such as an arm or a gear. The motor 213 is, for example, a DC motor, and is driven under the control of the light source control unit 211 to select a filter to be applied to the emitted light.

The signal processing unit 220 is a processing circuit such as a digital signal processor (DSP). The signal processing unit 220 performs various types of signal processing such as color separation, color interpolation, gain correction, white balance adjustment, and gamma correction on the imaging signal input from the electronic scope 100 and outputs the same to the image processing unit 230 on a subsequent stage.

The image processing unit 230 is a processing circuit such as a digital image processor (DSP). The image processing unit 230 generates image data by performing image processing such as scaling, color enhancement processing, and edge enhancement processing on the image signal input from the signal processing unit 220, and outputs the generated image data to the output unit 240 on the subsequent stage. The image processing unit 230 also calculates average brightness and the like of each pixel of the generated image data and outputs information of the calculated brightness to the control unit 201.

In this embodiment, the signal processing is executed on a prior stage of the image processing unit 230; however, it is also possible to configure such that the signal processing executed by the signal processing unit 220 and the image processing executed by the image processing unit 230 are executed in one processing circuit.

The output unit 240 is provided with a processing circuit such as a video processor. The output unit 240 converts the image signal input from the image processing unit 230 into a video signal compliant with a predetermined standard such as a National Television System Committee (NTSC) or a Phase Alternating Line (PAL). The output unit 240 sequentially outputs the converted video signal to the monitor device 300 to allow a display screen of the monitor device 300 to display the video of the object. In this embodiment, for example, in a case where the freeze button 124 of the electronic scope 100 is not pressed (or the freeze button 124 is released), the moving image is displayed on the monitor device 300, and in a case where the freeze button 124 is pressed, the still image is displayed on the monitor device 300.

The output unit 240 may also be configured to generate moving image data compressed by a predetermined moving image compression system from the image signal input from the image processing unit 230 and store the generated moving image data as a moving image file in the storage unit 202 under the control of the control unit 201. As the moving image compression system, MPEG-2, MPEG-4 (MPEG: Moving Picture Experts Group) or the like may be used. Furthermore, the output unit 240 may be configured to generate still image data such as Joint Photographic Experts Group (JPEG) data and Tagged Image File Format (TIFF) data from the image signal input from the image processing unit 230 and store the generated still image data in the storage unit 202 as a still image file under the control of the control unit 201.

Hereinafter, a method by which the CPU 153 of the electronic scope 100 controls the exposure time of the solid-state imaging device 152 is described. In this embodiment, a look-up table (LUT) storing control values for controlling the exposure time in the solid-state imaging device 152 is provided, and the CPU 153 controls the exposure time of the solid-state imaging device 152 with reference to the look-up table. Such lookup table should be stored in advance in the ROM 154, for example.

FIG. 3 is a conceptual diagram illustrating an example of the look-up table. The look-up table is a table in which a plurality of control values for controlling the exposure time of the solid-state imaging device 152 is stored in association with address values. The control values are set such that the exposure time decreases exponentially as the address value increases. More specifically, a relationship between the address value and the exposure time is determined such that the exposure time at a top address (address value 0) is set to 1/60 seconds and the exposure time becomes 0.99382 times each time the address value increases by 1. Note that, in the example illustrated in FIG. 3, the exposure time is illustrated in place of the control value for the sake of explanation, but actually, it is sufficient that the control value for controlling the exposure time of the solid-state imaging device 152 is stored.

For example, in a case of outputting a full HD image at 60 frames per second, a maximum value of the exposure time per frame is 1/60 seconds. In this embodiment, the maximum value of the exposure time is assigned to the top address (address value 0). At that time, in this embodiment, the exposure time of an address value n is set to $1/60 \times 0.99382^n$ seconds. That is, the exposure time is changed exponentially so that the brightness changes smoothly to human eyes.

An electronic shutter of the solid-state imaging device 152 may set the exposure time in horizontal synchronization signal (Hsync) units. Herein, the number of Hsyncs in one frame is determined by an output video period (for example, full HD_60p and the like) and the number of simultaneously output lines. For example, in a case where an image of full HD_60p is output simultaneously in two lines, 1126 Hsyncs are output simultaneously in two lines, so that 1126/2=563 Hsyncs are output. Therefore, since the maximum number of Hsyncs of the image of full HD_60p is 1126, there is no meaning in setting resolution of the electronic shutter of the solid-state imaging device 152 to 1126 or larger. Therefore, 1024 stages, the nearest as the power of 2 are appropriate as the resolution of the electronic shutter. Also, a minimum value of the exposure time in a case of outputting in full HD_60p is 1/1126 of 1/60 of 1 second. (that is, 1/67560 seconds).

However, in a case where the look-up table is configured assuming that the exposure time of the 1024th stage is 1/67560 seconds, a latter half of the table is rounded to substantially the same exposure time because of limitation of the resolution. Therefore, in this embodiment, the exposure time of the 1024th stage is set to, for example, 1/67560×2 seconds. For this reason, in this embodiment, the exposure time of the address value n is set to $1/60 \times 0.99382^n$ seconds.

Although the exposure time in a case of outputting the full HD image at 60 frames per second is described above, the exposure time for the address value n (n is an integer not smaller than 0) may be set as $1/N \times (a/H)^b$ in a case where the frame rate of the output image is set to N, the number of horizontal synchronization signals in one frame is set to H, and a constant larger than 1 is set to a. Herein, b is a value obtained by dividing the address value n by the maximum address value.

Hereinafter, a control procedure of the exposure time in the solid-state imaging device 152 is described.

Figure 4:
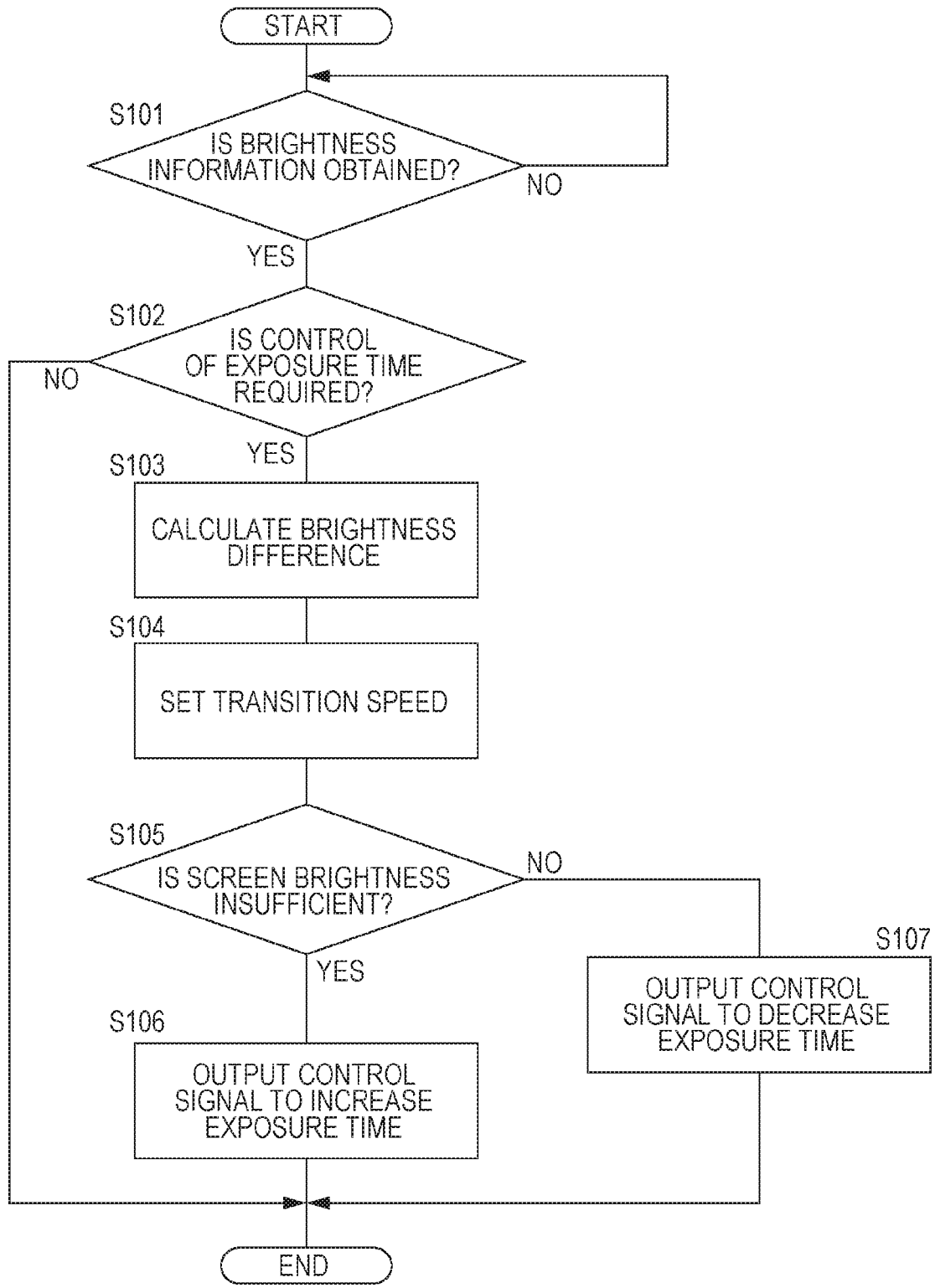
FIG. 4 is a flowchart for illustrating a procedure of processing executed by a control unit of a processor device.

FIG. 4 is a flowchart for illustrating a procedure of processing executed by the control unit 201 of the processor device 200. In a case where imaging by the solid-state imaging device 152 is started, the image signal is input to the image processing unit 230 via the AFE 156 on the electronic scope 100 side and the signal processing unit 220 on the processor device 200 side. The image processing unit 230 performs the image processing on the input image signal to generate the image data, and calculates the average brightness and the like of each pixel of the image data to output the information of the calculated brightness to the control unit 201. The average brightness calculated by the image processing unit 230 may be an average value of the brightness of an entire image or may be an average value of the brightness of a partial area of the image. This may also be an average value obtained by dividing the image into a plurality of areas and taking a weight into consideration for each area.

The control unit 201 of the processor device 200 determines whether the brightness information is obtained from the image processing unit 230 (step S101). In a case where the brightness information is not obtained (S101: NO), the control unit 201 stands by until the brightness information is obtained.

In a case where the brightness information is obtained (S101: YES), the control unit 201 determines whether it is necessary to control the exposure time on the basis of the obtained brightness information (step S102). For example, it is possible to set a threshold for the brightness value and determine whether the control of the exposure time is necessary according to a comparison result with the threshold. In a case where it is determined that the control of the exposure time is not necessary (S102: NO), the control unit 201 finishes the procedure by this flowchart.

In a case where it is determined that the control of the exposure time is necessary (S102: YES), the control unit 201 calculates a difference (brightness difference) between the current brightness of the image and the set brightness (step S103). Herein, the set brightness may be a value set in advance in the processor device 200 or may be an appropriate value set by the operator.

Next, the control unit 201 sets a speed (transition speed) to change the exposure time (step S104). For example, the control unit 201 may set the transition speed higher as the brightness difference calculated at step S103 is larger, and set the transition speed lower as the brightness difference calculated at step S103 is smaller.

Next, the control unit 201 determines whether screen brightness is insufficient (step S105). For example, in a case where the current brightness of the image is lower than the set brightness, the control unit 201 may determine that the screen brightness is insufficient. Also, in a case where the current brightness of the image is higher than the set brightness, the control unit 201 may determine that the screen brightness is excessive.

In a case where it is determined that the screen brightness is insufficient (S105: YES), the control unit 201 outputs a control signal to increase the exposure time to the CPU 153 of the electronic scope 100 (step S106).

In a case where it is determined that the screen brightness is not insufficient (S105: NO) and the screen brightness is excessive, the control unit 201 outputs a control signal to decrease the exposure time to the CPU 153 of the electronic scope 100 (step S107).

In the control signal transmitted by the control unit 201 at step S106 or step S107, a change request of the transition speed, information of the current screen brightness, information of the set brightness, and information of the calculated brightness difference may be included in addition to a change request of the exposure time.

Next, operation of the electronic scope 100 side is described.

Figure 5:
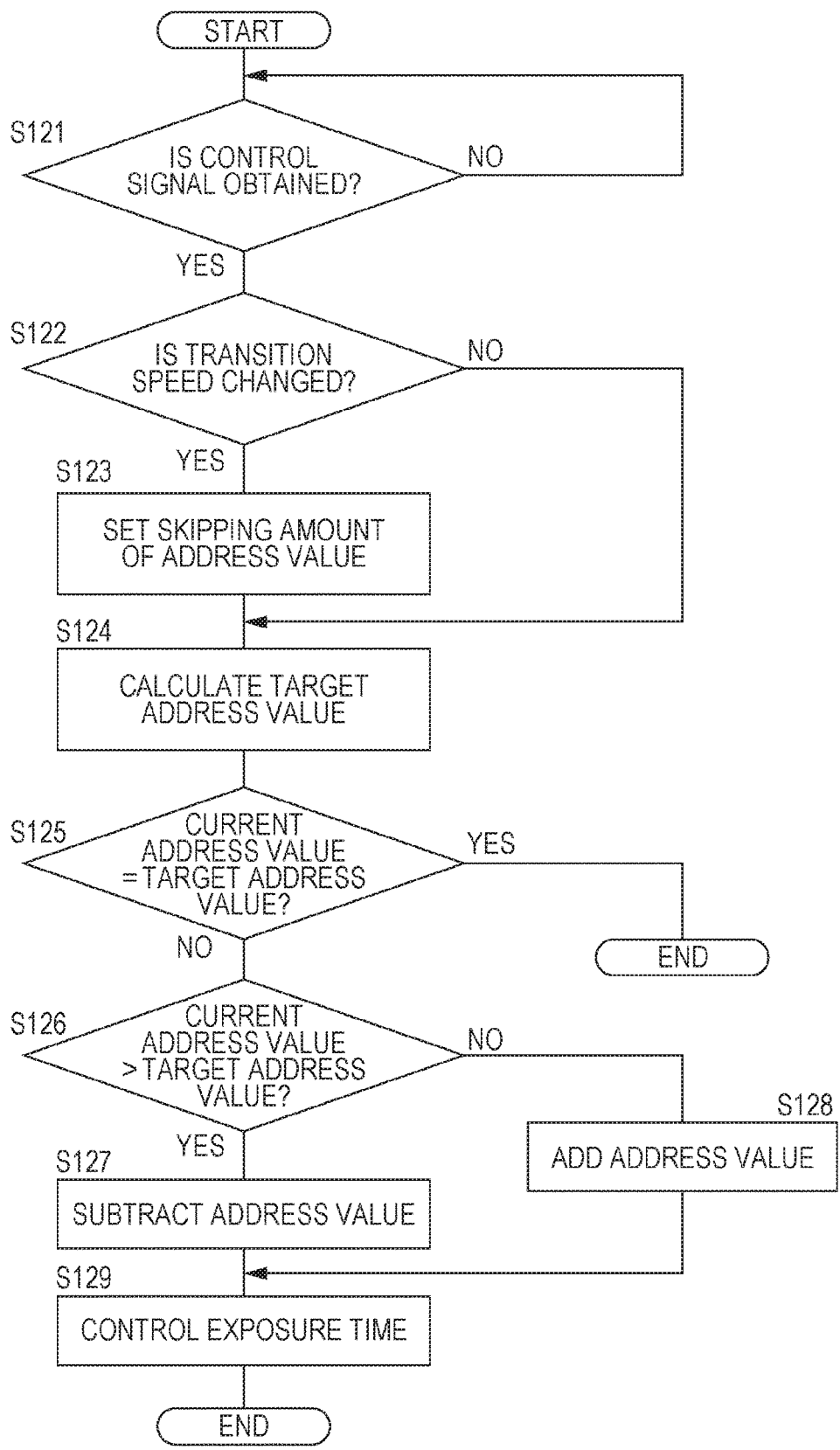
FIG. 5 is a flowchart for illustrating a procedure of processing executed by a CPU of an electronic scope.

FIG. 5 is a flowchart for illustrating a procedure of processing executed by the CPU 153 of the electronic scope 100. The CPU 153 determines whether the control signal for requesting a change of the exposure time is obtained from the control unit 201 (step S121). In a case where it is determined that the control signal is not obtained (S121: NO), the control unit 201 stands by until the control signal is obtained.

In a case where it is determined that the control signal requesting the change of the exposure time is obtained (S121: YES), the CPU 153 determines whether the obtained control signal includes the change of the transition speed (step S122).

In a case where it is determined that the change of the transition speed is included (S122: YES), the CPU 153 sets an amount (an increasing/decreasing amount) by which the address value is skipped (step S123). The amount by which the address value is skipped may be a value set in advance or an appropriate value set according to the transition speed.

In a case where it is determined at step S122 that the change of the transition speed is not included (S122: NO) or in a case where the amount by which the address value is skipped is set at step S123 (S123), the CPU 153 calculates a target address value (step S124). Herein, the target address value is an address value corresponding to the exposure time for realizing the set brightness.

Next, the CPU 153 determines whether the current address value is equal to the target address value (step S125). Herein, the current address value is an address value corresponding to the exposure time for realizing the current screen brightness. In a case where the current address value is equal to the target address value (S125: YES), the set brightness is realized, so that the CPU 153 finishes the procedure by this flowchart.

In a case where the current address value is not equal to the target address value (S125: NO), the CPU 153 determines whether the current address value is larger than the target address value (step S126).

In a case of determining that the current address value is larger than the target address value (S126: YES), the CPU 153 performs processing of subtracting the address value (step S127). At that time, in a case where a skipping amount of the address value is set at step S123, the CPU 153 subtracts by the skipping amount, and in a case where the skipping amount is not set, this subtracts by a predetermined amount (for example, 1).

On the other hand, in a case where the current address value is not equal to the target address value (S125: NO) and it is determined that the current address value is not larger than the target address value (S126: NO), that is, in a case where it is determined that the current address value is smaller than the target address value, the CPU 153 performs processing of adding the address value (step S128). At that time, in a case where the skipping amount of the address value is set at step S123, the CPU 153 adds the address value by the skipping amount, and in a case where the skipping amount is not set, this adds the address value by a predetermined amount (for example, 1).

Next, the CPU 153 reads the control value stored in the look-up table in association with the address value obtained by subtraction or addition from the ROM 154, and controls the exposure time of the solid-state imaging device 152 on the basis of the read control value (step S129).

As described above, in this embodiment, since the exposure time in the solid-state imaging device 152 may be controlled exponentially, it is possible to realize smooth brightness transition along with human sense. Also, since the transition speed for changing the screen brightness may be flexibly set, exposure adjustment with a high real-time property may be realized.

Note that, although it is configured that the processor device 200 determines the necessity of controlling the exposure time in this embodiment, it is also possible that the brightness information is output from the processor device 200 to the CPU 153 of the electronic scope 100 and the CPU 153 of the electronic scope 100 determines the necessity of the exposure time. Also, although it is configured that the CPU 153 of the electronic scope 100 reads the control value for controlling the exposure time with reference to the look-up table in this embodiment, it is also possible that the storage unit 202 of the processor device 200 has the look-up table, the control unit 201 reads the control value for controlling the exposure time, and the read control value is output to the CPU 153 of the electronic scope 100.

Also, although it is configured that the control value is read with reference to the look-up table in this embodiment, it is also possible that a function defining the relationship between the address value and the control value is set, and the exposure time of the solid-state imaging device 152 is controlled on the basis of the control value output from the function when the address value is input.

It should be understood that the embodiment disclosed herein as illustrative in all respects and not restrictive. The scope of the present invention is indicated not by the meaning described above but by the scope of claims, and it is intended that all modifications within the scope of claims and equivalent thereof are included.

REFERENCE SIGNS LIST

100 Electronic scope
152 Solid-state imaging device (imaging device)
153 CPU (control unit)
153 RCM (storage unit)
200 Processor device
201 Control unit
202 Storage unit
203 Operation unit
210 Connector
211 Light source control unit
212 Light source
220 Signal processing unit
230 Image processing unit (brightness calculation unit)
240 Output unit

The invention claimed is:

1. An electronic endoscope device for obtaining an imaging signal from a solid state imaging device for imaging an object and outputting an image based on the obtained imaging signal, the electronic endoscope device comprising:
   an image processor and an image memory which stores an instruction, wherein when the image processor executes the instruction stored in the image memory, the image processor operates as a brightness calculator that calculates brightness of the image;
   a controller that changes an exposure time in the solid state imaging device so that the brightness calculated by the brightness calculator approaches a predetermined brightness; and
   a storage medium that stores a plurality of control values for controlling the exposure time of the solid state imaging device in association with address values indicating respective storage sites; wherein:
   the plurality of control values is arranged such that the exposure time changes with respect to the address values, and
   the controller calculates a current address value corresponding to the brightness calculated by the brightness calculator and a target address value corresponding to the predetermined brightness,
   the controller sequentially increases or decreases the current address value for reading a control value of the plurality of control values from the storage medium until the current address value reaches the target address value corresponding to the predetermined brightness, and
   the controller sequentially specifies an address value in the storage medium and reads a control value of the plurality of control values for the solid state imaging device, and controls the exposure time of the solid state imaging device on the basis of the read control value.

2. The electronic endoscope device according to claim 1, wherein the controller
calculates a difference between the brightness calculated by the brightness calculation calculator and the predetermined brightness, and sets an increasing/decreasing amount by which the current address value is increased or decreased according to the calculated difference.

3. The electronic endoscope device according to claim 2, wherein, a frame rate of the image based on the imaging signal is set to N, the number of horizontal synchronization signals in one frame is set to H, an arbitrary constant larger than 1 is set to a, the current address value is set to n (n is an integer not smaller than 0), and a value obtained by dividing the current address value n by a maximum value of the current address value is set to b,
the exposure time for the current address value n is set to $1/N \times (a/H)^b$.

4. The electronic endoscope device according to claim 1, wherein, a frame rate of the image based on the imaging signal is set to N, the number of horizontal synchronization signals in one frame is set to H, an arbitrary constant larger than 1 is set to a, the current address value is set to n (n is an integer not smaller than 0), and a value obtained by dividing the current address value n by a maximum value of the current address value is set to b,
the exposure time for the current address value n is set to $1/N \times (a/H)^b$.

* * * * *